(12) United States Patent
Isogai et al.

(10) Patent No.: US 7,703,920 B2
(45) Date of Patent: Apr. 27, 2010

(54) OPHTHALMIC APPARATUS

(75) Inventors: Naoki Isogai, Nishio (JP); Kazuhiro Yoshimura, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 12/320,636

(22) Filed: Jan. 30, 2009

(65) Prior Publication Data

US 2009/0195750 A1 Aug. 6, 2009

(30) Foreign Application Priority Data

Feb. 1, 2008 (JP) .............................. 2008-023170
Jan. 28, 2009 (JP) .............................. 2009-016371

(51) Int. Cl.
*A61B 3/14* (2006.01)
*A61B 3/00* (2006.01)

(52) U.S. Cl. ..................... 351/208; 351/206; 351/245

(58) Field of Classification Search ................. 351/200, 351/205, 206, 208, 245
See application file for complete search history.

(56) References Cited

U.S. PATENT DOCUMENTS

| 5,463,430 | A | 10/1995 | Isogai et al. |
| 5,644,375 | A | 7/1997 | Suzuki |
| 5,689,325 | A | 11/1997 | Isogai et al. |
| 5,909,269 | A | 6/1999 | Isogai et al. |
| 6,145,990 | A | 11/2000 | Uchida |
| 6,685,318 | B2 * | 2/2004 | Kohayakawa ............ 351/208 |
| 7,338,172 | B2 | 3/2008 | Yoshimura et al. |

| 2002/0018179 | A1 | 2/2002 | Hayashi et al. |
| 2003/0025875 | A1 | 2/2003 | Kohayakawa |
| 2004/0114107 | A1 | 6/2004 | Mimura |
| 2005/0185137 | A1 | 8/2005 | Yoshimura et al. |

FOREIGN PATENT DOCUMENTS

| GB | 2 293 659 A | 4/1996 |
| JP | A-6-46999 | 2/1994 |
| JP | A-8-98808 | 4/1996 |
| JP | A-8-280627 | 10/1996 |
| JP | A-10-216089 | 8/1998 |
| JP | A-2004-174155 | 6/2004 |
| JP | A-2005-211351 | 8/2005 |
| JP | A-2005-224257 | 8/2005 |
| JP | A-2006-280612 | 10/2006 |

* cited by examiner

*Primary Examiner*—Jack Dinh
(74) *Attorney, Agent, or Firm*—Oliff & Berridge PLC

(57) ABSTRACT

An ophthalmic apparatus capable of alignment in total automation and manual alignment with an examinee's eye comprising an ophthalmic examination unit, a unit detecting an alignment state of the examination unit with the eye, a main base, a mobile base on which the examination unit is mounted and moved horizontally on the main base through operation of a control member, driving mechanisms moving the examination unit vertically and horizontally with respect to the mobile base, means switching a mode between a manual mode of performing alignment of the examination unit with each eye in sequence through the operation and a fully automatic mode of performing the alignment through driving of the driving mechanisms, and a control unit controlling the driving based on the detection result which starts in the fully automatic mode the driving based on a predetermined trigger signal so as to perform the alignment.

5 Claims, 5 Drawing Sheets

OPHTHALMIC APPARATUS

BACKGROUND OF THE INVENTION

1. Field of the Invention

The present invention relates to an ophthalmic apparatus which performs examination or measurement of an examinee's eye.

2. Description of Related Art

For an ophthalmic apparatus which performs alignment of an ophthalmic examination unit with respect to an examinee's eye and performs examination of the eye, there is known an ophthalmic apparatus comprising an alignment mechanism which is provided in order to mechanically perform horizontal movement of a mobile base on which an ophthalmic examination unit is mounted with respect to a fixed main base. In addition, there is known an ophthalmic apparatus arranged to perform automatic precise alignment after manual rough alignment by comprising a driving mechanism capable of moving an ophthalmic examination unit independently in a back/forth direction, aright/left direction and an up/down direction with respect to a mobile base on which the ophthalmic examination unit is mounted (see Japanese Patent Application Unexamined Publication No. Hei08-98808). In the apparatus having such a configuration, a movable range of the driving mechanism extends only for 5 mm both in the back direction and the forth direction and both in the right direction and the left direction from a reference position (for 16 mm both in the up direction and the down direction).

In recent years, there is known an apparatus in which a movable range of a driving mechanism arranged to move an ophthalmic examination unit with respect to examinee's eyes is established to be more than a pupillary distance between the eyes for the purpose of total automation of alignment including rough alignment. In this case, the alignment of the ophthalmic examination unit with respect to each eye is automatically performed in sequence (see Japanese Patent Application Unexamined Publication No. Hei10-216089).

However, even in the case of the alignment including the rough alignment in total automation, automatic measurement of each eye cannot be made for every type of examinee. For example, if the eye involuntarily moves very rapidly, the movement of the ophthalmic examination unit by the driving mechanism sometimes cannot track the movement of the eye. In preparation for such a case that an examinee has an eye on which the automatic alignment is difficult to be performed, the above-described apparatus is equipped with an electric control member (e.g., an electric joystick, a trackball) which is operated by an examiner. The driving mechanism is driven and controlled in accordance with an amount and a direction of the operation of the control member, and thereby alignment of the ophthalmic examination unit with respect to the eye can be performed manually. However, the manual alignment using the electric control member is difficult in the operation of the control member, which could take time and trouble to perform alignment tasks.

SUMMARY OF THE INVENTION

An object of the invention is to overcome the problems described above and to provide an ophthalmic apparatus which is capable of preferably performing alignment in total automation and manual alignment with respect to an examinee's eye.

To achieve the objects and in accordance with the purpose of the present invention, an ophthalmic apparatus comprising an ophthalmic examination unit arranged to perform examination of an examinee's eye, an alignment state detection unit arranged to detect an alignment state of the ophthalmic examination unit with respect to the eye, the alignment state detection unit comprising a photographing optical system arranged to photograph an anterior segment of the eye and placed in the ophthalmic examination unit, a main base, a mobile base on which the ophthalmic examination unit is mounted, the mobile base arranged to be moved in a horizontal direction on the main base through operation of a control member by an examiner, a vertical driving mechanism arranged to move the ophthalmic examination unit vertically with respect to the mobile base through driving of a motor, a horizontal driving mechanism arranged to move the ophthalmic examination unit horizontally with respect to the mobile base through driving of a motor, a movable range in a right/left direction of the horizontal driving mechanism being established to be more than a predetermined pupillary distance, mode changeover means arranged to switch a mode between a manual mode of performing alignment of the ophthalmic examination unit with respect to each right and left eye in sequence through the operation of the control member and a fully automatic mode of performing the alignment through driving of the driving mechanisms, and a control unit arranged to control the driving of the driving mechanisms based on a detection result by the alignment state detection unit, wherein the control unit starts, in a case where the fully automatic mode is established by the mode changeover means, the driving of the driving mechanisms based on a predetermined trigger signal which is emitted when the mobile base is placed at a predetermined position on the main base so as to perform the alignment.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate an embodiment of the present invention and, together with the description, serve to explain the objects, advantages and principles of the invention. In the drawings.

DETAILED DESCRIPTION OF THE PREFERRED EMBODIMENTS

Figure 1:
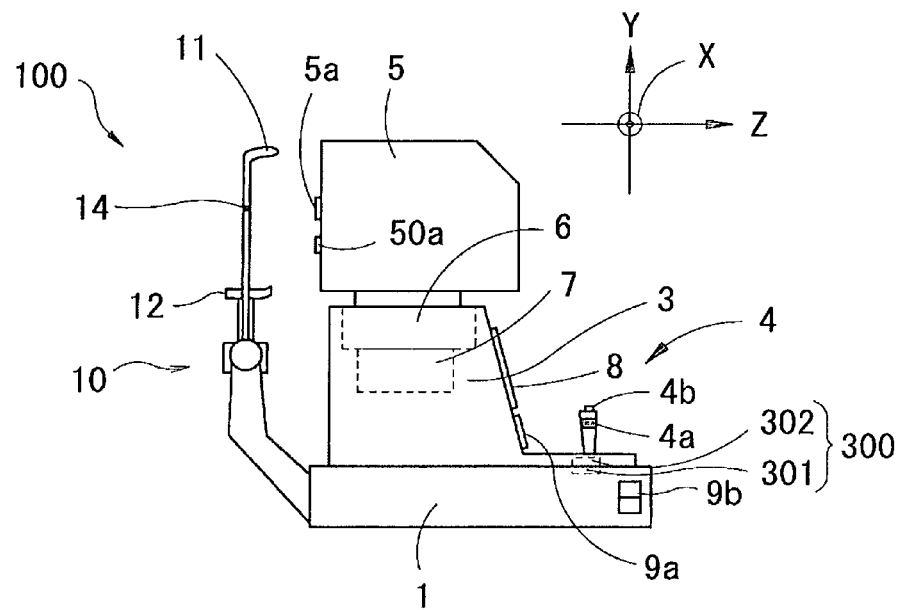
FIG. 1 is a schematic external view showing an ophthalmic apparatus according to a preferred embodiment of the present invention.

A detailed description of an ophthalmic apparatus according to a preferred embodiment of the present invention is provided below with reference to the accompanying drawings. FIG. 1 is a schematic external view showing the ophthalmic apparatus according to the preferred embodiment of the present invention.

An ophthalmic apparatus 100 comprises a main base 1 to which a face supporting unit 10 for fixing a face of an examinee is fixed. The face supporting unit 10 comprises a forehead rest 11 with which a forehead of the examinee is brought into contact, and a chin rest 12 on which a chin of the examinee is rested. The chin rest 12 is moved in an up/down direction (a Y-direction) by a chin rest movement mechanism 30 to be described later. Eye level markers 14 provided in columns of the forehead rest 11 are used as targets for adjustment of height of eyes (eye level) of the examinee which is performed by moving up and down the chin rest 12. When the eye level is adjusted such that the height of the examinee's eyes is brought to the same level as the eye level markers 14, the examinee's face is firmly fixed by the forehead rest 11 and the chin rest 12.

A mobile base 3 is arranged to be movable (slidable) in a horizontal direction (X- and Z-directions) on the fixed main base 1 by a sliding mechanism (not shown). An ophthalmic examination unit 5 is mounted on the mobile base 3, and houses an optical system for ophthalmic examination and other systems. The sliding mechanism is used as a manual movement mechanism for moving the mobile base 3 with respect to the fixed main base 1 through manual operation of a joystick 4 provided on the mobile base 3.

In this case, the sliding mechanism is arranged such that a movable range in a right/left direction (an X-direction) of the mobile base 3 is established to be more than a pupillary distance between the eyes of the examinee so that alignment of the ophthalmic examination unit 5 with respect to each eye can be performed in sequence through movement in the X-direction of the mobile base 3. Hence, the movable range can satisfy a movable range required for a fully automatic mode to be described later. In this case, it is preferable that the movable range is arranged to have an extra range in addition to an amount of the movement in the X-direction which corresponds to the pupillary distance so that the ophthalmic examination unit 5 is moved smoothly without reaching a movement limiting position in the X-direction during automatic alignment. To be specific, the movable range is arranged to extend for about 45 mm both in the right direction and the left direction from a horizontal center position, and thus the horizontal movable range of about 90 mm in total is established as a movable range of the mobile base 3 in the fully automatic mode. Accordingly, the automatic alignment is performed smoothly on an examinee with eyes a pupillary distance of which is large.

In addition, a movable range in a back/forth direction (the Z-direction) of the mobile base 3 is established to be a range such that alignment in a back/forth (working distance) direction of the ophthalmic examination unit 5 with respect to the eyes is possible independently of a position of the examinee. Further, the movable range in the Z-direction is arranged to have an extra movement range in the back direction in addition to the movement range used in the alignment with respect to the eyes in order to prevent the ophthalmic examination unit 5 from being brought into contact with a nose or other parts of the examinee at the time of switching the eye to be measured between the right and left eyes. To be specific, the movable range of about 40 mm in the Z-direction which includes the movement range that the alignment in the Z-direction with respect to the eyes is possible can be established as a movable range of the mobile base 3 in the fully automatic mode.

The apparatus according to the preferred embodiment of the present invention is arranged such that the sliding mechanism and an XZ driving unit 7 which are used as a movement mechanism for horizontally moving the ophthalmic examination unit 5 with respect to the eyes have their respective movable ranges in the X-direction so that the alignment with respect to each eye in sequence through operation of the sliding mechanism and the alignment with respect to each eye in sequence through operation of the XZ driving unit 7 can be individually performed in accordance with the pupillary distance, and have their respective movable ranges in the X- and Z-directions so that the alignment in the Z-direction with respect to each eye in sequence can be performed and that the ophthalmic examination unit 5 can be prevented from being brought into contact with the nose of the examinee.

For the sliding mechanism used as the manual movement mechanism, a known sliding mechanism which comprises a right/left sliding mechanism for sliding the mobile base 3 right and left with respect to the main base 1 and a back/forth sliding mechanism for sliding the mobile base 3 back and forth with respect to the main base 1 and is capable of horizontally moving the mobile base 3 with respect to the main base 1 is preferably used.

The ophthalmic examination unit 5 is provided with an examination window 5a through which the examinee looks inside a housing of the ophthalmic examination unit 5, and light from an ophthalmic examination optical system in the housing is projected onto the eyes through the examination window 5a. A photographing window 50a is a window of a second photographing optical system 50 arranged to photograph the eyes and peripheries thereof simultaneously. The second photographing optical system 50 has a photograph region such that at least the eyes and the eye level markers 14 in the vicinity thereof can be photographed simultaneously in a state where the eyes and the apparatus are placed to have a predetermined positional relationship.

A Y driving unit 6 is arranged to move the ophthalmic examination unit 5 in the up/down direction (the Y-direction), and the XZ driving unit 7 is arranged to move the ophthalmic examination unit 5 in the right/left direction (the X-direction) and in the back/forth direction (the Z-direction). The Y driving unit 6 and the XZ driving unit 7 are incorporated into the mobile base 3. When the Y driving unit 6 and the XZ driving unit 7 are driven, the ophthalmic examination unit 5 is moved in the X-, Y- and Z-directions with respect to the mobile base 3. Consequently, the ophthalmic examination unit 5 can be moved in the three dimensional directions with respect to the eyes. For the Y driving unit 6 and the XZ driving unit 7, a driving unit having a configuration such that a sliding mechanism for moving the ophthalmic examination unit 5 is moved through driving of a motor is preferably used.

The joystick 4 is provided on the mobile base 3, and is operated manually by an examiner so as to adjust the ophthalmic examination unit 5 to a given position with respect to the examinee's eye. When the joystick 4 is operated back and forth and right and left, the mobile base 3 is moved in the X- and Z-directions (the horizontal direction) with respect to the main base 1 by the above-described sliding mechanism, and the ophthalmic examination unit 5 is consequently moved in the X- and Z-directions with the eye. When a rotation knob 4a of the joystick 4 is rotated and operated, the Y driving unit 6 is driven to move the ophthalmic examination unit 5 in the Y-direction (a vertical direction). When a measurement starting switch 4b provided at the top of the joystick 4 is pressed, a trigger signal for starting measurement and photographing by the ophthalmic examination optical system is emitted. A display monitor 8 and a control section 9a which is used for performing setting of measurement conditions and other factors are provided at the examiner's side of the mobile base 3. A chin rest switch 9b (an up/down switch) used for moving the chin rest 12 up and down through operation by the examiner is provided on a side face of the main base 1 at the examiner's side. When the chin rest switch 9b is pressed, the chin rest movement mechanism 30 is driven in accordance with the direction of the operation, and the height of the chin rest 12 is adjusted.

Figure 2:
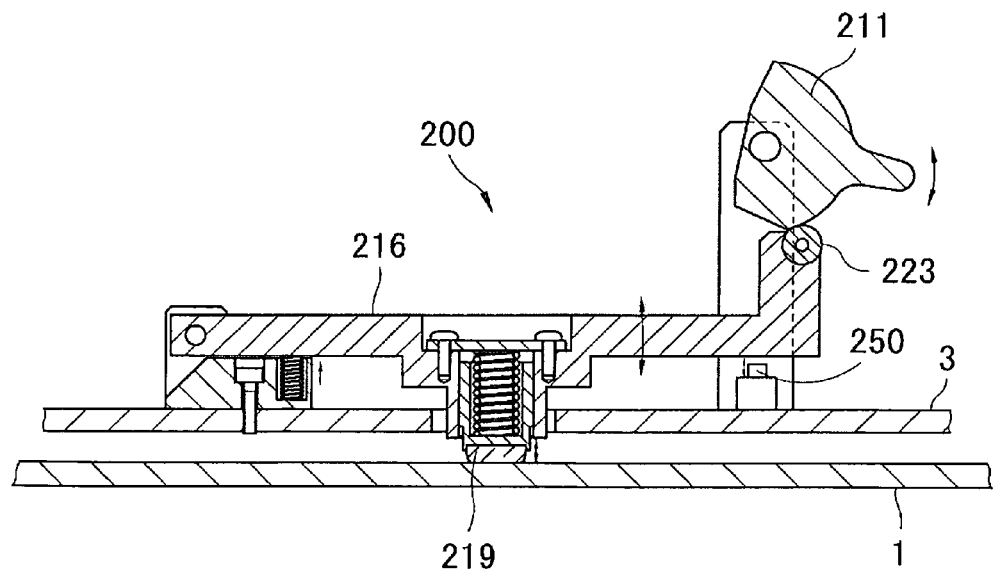
FIG. 2 is a view showing a lock mechanism in the ophthalmic apparatus.

FIG. 2 is a view showing a lock mechanism in the ophthalmic apparatus according to the preferred embodiment of the present invention. A lock mechanism 200 is arranged to lock the mobile base 3 to the fixed main base 1. The lock mechanism 200 is provided with a switching mechanism with which the mobile base 3 is switched between a state of being locked to the fixed main base 1 and a state of being unlocked therefrom. Hence, with the switching mechanism, it is possible to arbitrarily switch the locked state and the unlocked state.

To be more specific, for the lock mechanism 200, a lock mechanism is preferably used which comprises an arm 216 which is pivotally supported by the mobile base 3 so as to be rotatable in the up/down direction, a locking member 219 which is held by the arm 216 and is pushed to the main base 1, an operation member 211 which is arranged to rotate the arm 216 in order to move the locking member 219 between a first position where the locking member 219 is apart from the main base 1 and a second position where the locking member 219 is pushed to the main base 1, and which is placed at a position farther than the locking member 219 with respect to a distance from the rotation center of the arm 216, and a rotation limiting member 223 which is arranged to limit the rotation of the arm 216 when the locking member 219 is moved to the first position or the second position through the operation of the operation member 211. The mobile base 3 is unlocked when the operation member 211 is raised by the examiner while the mobile base 3 is locked when the operation member 211 is lowered by the examiner. Besides, in the above described lock mechanism, the mobile base 3 could be moved by applying excessive force to the mobile base 3; however, it is essential only that the movement of the mobile base 3 should be locked in normal use (e.g., normal tilting operation of the joystick 4) (for the details, see Japanese Patent Application Unexamined Publication No. 2005-224257 corresponding to U.S. Pat. No. 7,338,172 by the same applicant).

In addition, the above-described lock mechanism 200 is provided with a lock detection unit 250 arranged to detect the lock of the mobile base 3 by the lock mechanism 200. A signal of the detection is outputted to a control unit 70.

To be more specific, for the lock detection unit 250, a micro-switch is attached to a bottom face of the mobile base 3. It is arranged such that when the operation member 211 is lowered and the arm 216 is rotated to be moved down, the micro-switch is pushed by a lower section of the arm 216 and emits the detection signal which is outputted to the control unit 70 to be described later. Based on the detection signal, the control unit 70 judges that the mobile base 3 is locked to the fixed main base 1.

Meanwhile, it is arranged such that when the operation member 211 is raised and the arm 216 is rotated to be moved up, the micro-switch is released from the state of being pressed by the arm 216 and stops emitting the detection signal which is outputted to the control unit 70. Based on this, the control unit 70 judges that the mobile base 3 is unlocked from the fixed main base 1. That is, the control unit 70 is capable of detecting the switching of the mobile base 3 between the state of being locked to the fixed main base 1 and the state of being unlocked therefrom.

Figure 3:
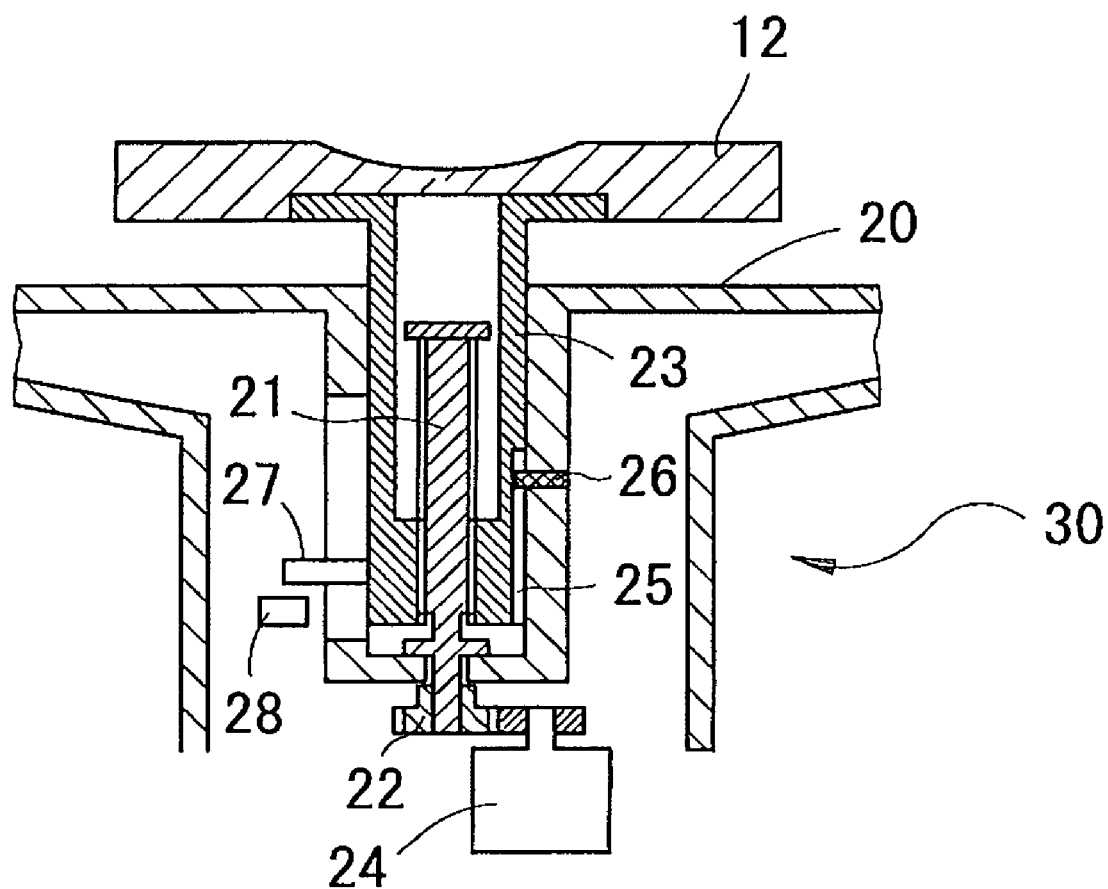
FIG. 3 is a schematic sectional view showing a configuration of a chin rest movement mechanism in the ophthalmic apparatus.

FIG. 3 is a schematic sectional view showing a configuration of the chin rest movement mechanism 30 which is arranged to electrically move the chin rest 12 up and down. In a support base 20, a lead screw 21 is provided to stand. A column 23 having a female screw to mate with the lead screw 21 is attached to the support base 20 so as to be movable up and down while guided by the support base 20. The chin rest 12 is provided on the top of the column 23 and fixed thereto. A gear 22 is provided to the lead screw 21 on the lower side, and a gear at the side of a pulse motor 24 meshes with the gear 22. The column 23 is provided with flutes 25, and the flutes 25 and a bis 26 for antirotation purposes prevent the column 23 from being rotated. The lead screw 21 is rotated by rotation of the motor 24, whereby the column 23 and the chin rest 12 are moved up and down. A shielding plate 27 is attached to the column 23 on the lower side, and a photosensor 28 arranged to detect the shielding plate 27 is provided at the side of the support base 20. The photosensor 28 detects that the chin rest 12 is lowered to its lower limit by detecting the shielding plate 27. In addition, the height of the chin rest 12 can be detected by counting the pulse number which is given to the pulse motor 24 with reference to the lower limit of the chin rest 12 which is detected by the photosensor 28. Accordingly, it is also possible to adjust the chin rest 12 to a given height (an initial position).

Figure 4:
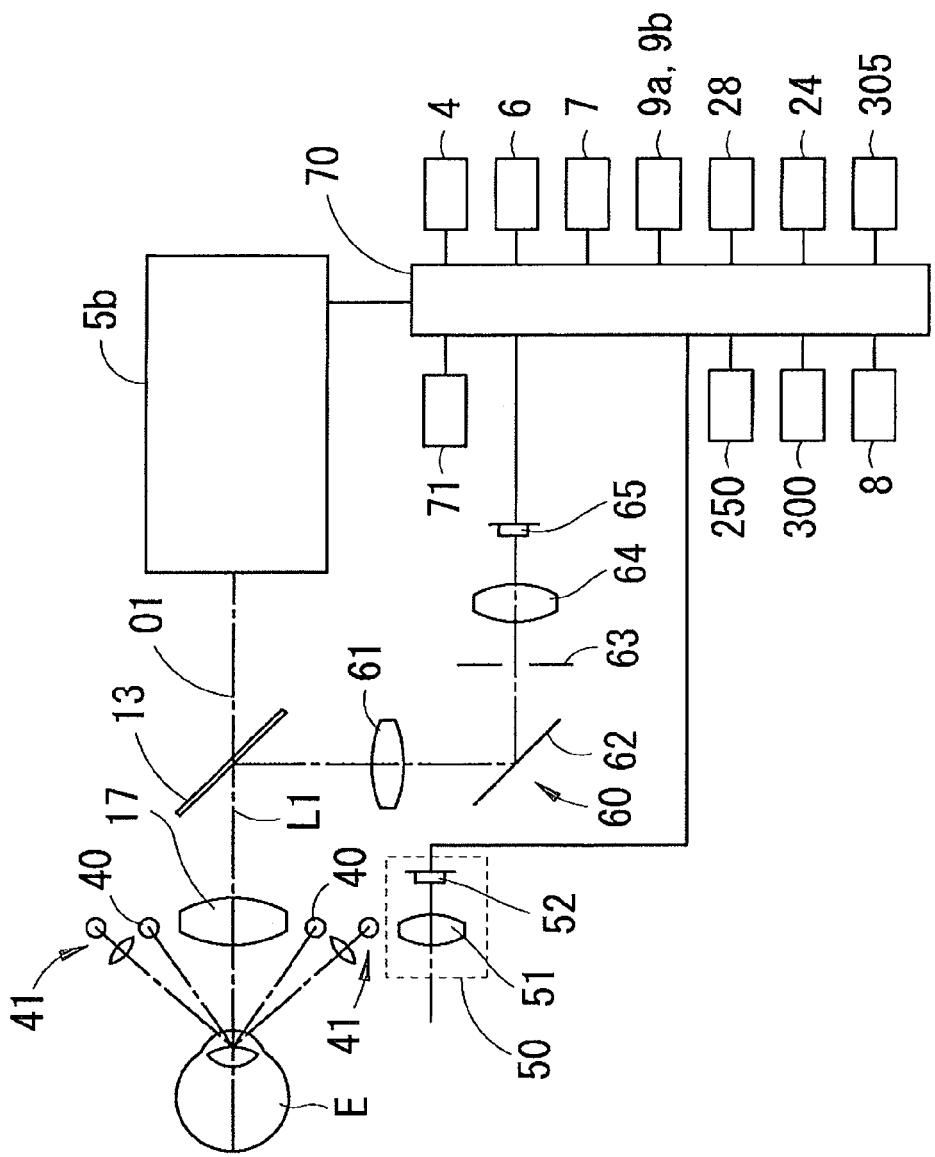
FIG. 4 is a view showing a schematic configuration of an optical system and a control system provided in an ophthalmic examination unit of the ophthalmic apparatus.

FIG. 4 is a view showing a schematic configuration of an optical system and a control system provided in the ophthalmic examination unit 5. An objective lens 17, a beam splitter 13 and an ophthalmic examination optical system 5b are placed on an optical path O1, and light emitted from the ophthalmic examination optical system 5b enters an examinee's eye E via the beam splitter 13 and the objective lens 17. Reflection light from the eye E enters the ophthalmic examination optical system 5b via the objective lens 17 and the beam splitter 13, and given eye characteristics (e.g., eye refractive power, an image of a fundus, an image of an anterior segment) are obtained. An optical axis L1 is an optical axis of the objective lens 17 and doubles as an optical axis of the ophthalmic examination optical system 5b and an optical axis of a first photographing optical system 60 to be described later.

A ring target projection optical system 40 which is arranged to emit near infrared light for projecting a ring target onto a cornea Ec of the eye E and a target projection optical system 41 for working distance detection which is arranged to emit near infrared light for detecting an alignment state in the Z-direction with respect to the eye E are placed in front of an anterior segment of the eye E so as to be laterally symmetrical with respect to the optical axis L1 (in FIG. 4, they are shown to be vertically symmetrical for the sake of illustration). The projection optical system 41 is arranged to project an infinite target onto the cornea Ec of the eye E. The projection optical system 40 is used also as an anterior-segment illumination which illuminates the anterior segment of the eye E.

In addition, a photographing optical system for an anterior segment of an eye which is arranged to photograph the anterior segment of the eye E comprises the first photographing optical system 60 which is arranged to photograph the anterior segment, and the second photographing optical system 50 which is arranged to photograph the anterior segments and peripheral regions thereof. The second photographing optical system 50 comprises a lens 51 and a two-dimensional photodetector 52, and is arranged to photograph the anterior segments under magnification lower than the first photographing optical system 60 (see FIG. 6). Reflection light from the anterior segments illuminated with the infrared light is photo-received on the two-dimensional photodetector 52 via the lens 51. An output of the two-dimensional photodetector 52 is sent to the control unit 70 to be described later.

Figure 6:
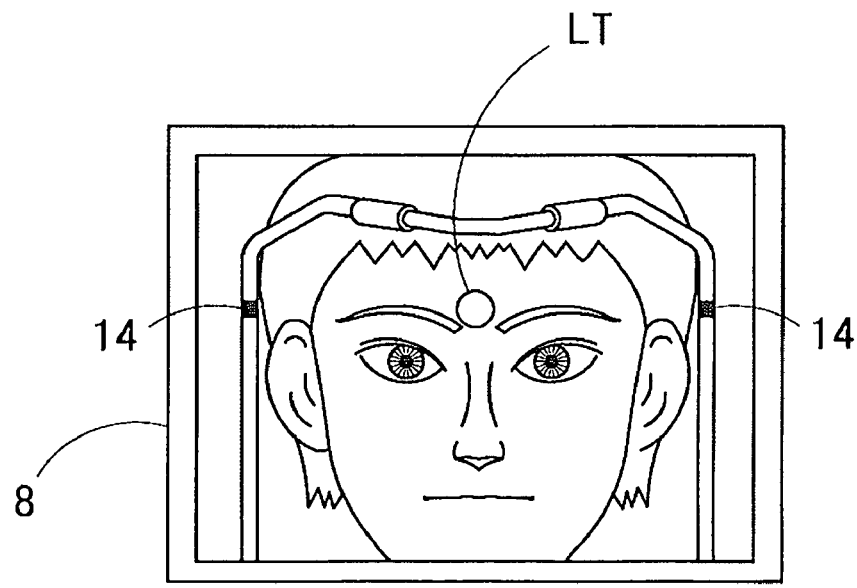
FIG. 6 is a view showing an example of a broad image of anterior segments of eyes displayed on a display monitor.

In the preferred embodiment of the present invention, the second photographing optical system 50 is placed immediately below the objective lens 17 (see FIG. 4), and is arranged to have the photograph region that both of the eyes and the right and left eye level markers 14 can be photographed simultaneously (see FIG. 6). Accordingly, a check of the height of the examinee's eyes, a judgment of the eyes whether the right eye or the left eye, and location of the positions of the right and left eyes can be made simultaneously.

Figure 7:
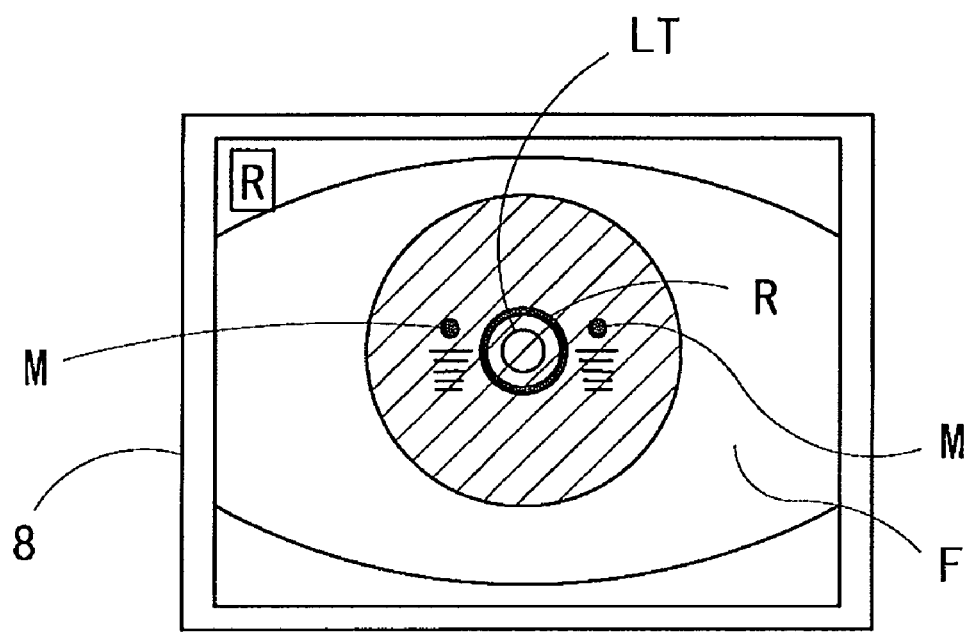
FIG. 7 is a view showing an example of a high-magnification image of the anterior segment of the eye displayed on the display monitor.

The first photographing optical system 60 is placed in a reflecting direction of the beam splitter 13, and comprises a relay lens 61, a total reflection mirror 62, a diaphragm 63, an image-pickup lens 64 and a two-dimensional photodetector 65. An image of the examinee's eye is picked up by the two-dimensional photodetector 65 under high magnification, and an image of the alignment target which is projected onto the cornea of the examinee's eye by the target projection optical systems 40 and 41 is detected (see FIG. 7). In the above-described optical systems, the reflection light from the anterior segment illuminated with the infrared light is photo-received on the two-dimensional photodetector 65 via the objective lens 17, the beam splitter 13, and the relay lens 61 to the image-pickup lens 64. An output of the two-dimensional photodetector 65 is sent to the control unit 70 to be described later. In the apparatus according to the preferred embodiment of the present invention, it is arranged that the ophthalmic examination unit 5 comes to the middle of the movable range in the up/down direction when the optical axis L1 and the eye level markers 14 are adjusted in height.

Next, a description of the control system will be provided. The control unit 70 performs control of the entire apparatus. The control unit 70 is connected with the display monitor 8 and controls a display screen of the display monitor 8. In addition, the control unit 70 detects a relative position between the examinee's eye and the ophthalmic examination unit 5 based on the position of the alignment target image picked up by the first photographing optical system 60 or the second photographing optical system 50 (alternatively, based on the position of the eye). The control unit 70 is connected with the ophthalmic examination optical system 5b, the photodetector 65, the photodetector 52, the Y driving unit 6, the XZ driving unit 7, the motor 24, the photosensor 28, the joystick 4, the control section 9a, the chin rest switch 9b, a memory 71, the lock detection unit 250, a position detection unit 300 to be described later, a micro-switch 305 and other elements.

The micro-switch 305 plays a role of detection means arranged to detect that the mobile base 3 is moved to a predetermined position through the movement in the back/forth direction of the mobile base 3 with respect to the main base 1, and a detection signal from the micro-switch 305 is used as a switching signal for switching an image of the anterior segment(s) displayed on the display monitor 8 between the anterior-segment image picked up by the first photographing optical system 60 and the anterior-segment image picked up by the second photographing optical system 50.

The main base 1 is provided with a guide plate (not shown) which is arranged to push up the micro-switch 305 causing the detection signal to be outputted therefrom when the mobile base 3 is moved to the predetermined position in the back/forth direction. For the above-described detection mechanism, a photo sensor is preferably used, or a potentiometer or other detecting elements are preferably used such that position detection is made based on a result which is detected as the need arises.

An alignment mode of performing alignment of the ophthalmic examination unit 5 with respect to the examinee's eye can be switched between an automatic alignment mode and a manual alignment mode. When the automatic alignment mode (hereinafter, referred to simply as the fully automatic mode) is established, the control unit 70 detects the relative positions between the examinee's eyes and the ophthalmic examination unit 5 while the mobile base 3 is locked to the main base 1. Then, based on a result of the detection, the control unit 70 controls the Y driving unit 6 and the XZ driving unit 7 to move the ophthalmic examination unit 5, and performs the alignment of the ophthalmic examination unit 5 with respect to each eye in sequence. When the manual alignment mode (hereinafter, referred to simply as the manual mode) is established, the ophthalmic examination unit 5 is adjusted to the eye by moving the mobile base 3. To be specific, the examiner locates the position of the eye while looking at the anterior-segment image displayed on the display monitor 8, and performs the alignment of the ophthalmic examination unit 5 with respect to the eye through the operation of the joystick 4. A mode changeover switch with which the mode is manually switched between the fully automatic mode and the manual mode is provided to the control section 9a.

In the preferred embodiment of the present invention, the alignment in the fully automatic mode is performed while the mobile base 3 is locked onto the fixed main base 1 at a predetermined position (e.g., a lateral center position which is at a rearmost edge) by the lock mechanism 200. The alignment in the manual mode is performed while the mobile base 3 is unlocked from the fixed main base 1 by the lock mechanism 200. In addition, when the fully automatic mode is established, the control unit 70 controls the second photographing optical system 50 to pick up a broad image of the examinee's face, locates the positions of the right and left eyes based on a signal from the image, and performs thereby the automatic alignment of the ophthalmic examination unit 5 with respect to each eye.

Further, the manual mode can be switched between a manual mode and a semi-manual mode. When the manual mode (a first manual mode) is established, the control unit 70 prohibits the XZ driving unit 7 to move the ophthalmic examination unit 5. In this case, by moving the mobile base 3 and moving up and down the ophthalmic examination unit 5 through manual operation of the joystick 4, the ophthalmic examination unit 5 is adjusted to the eye. When the semi-manual mode (a second manual mode) is established, the control unit 70 detects the relative position between the eye and the ophthalmic examination unit 5. Then, the control unit 70 controls the XZ driving unit 7 to move the ophthalmic examination unit 5 within the movable range which is limited by the control unit 70 based on a result of the detection. In this case, the ophthalmic examination unit 5 is adjusted to the eye by the horizontal movement of the ophthalmic examination unit 5 by the XZ driving unit 7 within the limited range in addition to the movement of the mobile base 3 and the vertical movement of the ophthalmic examination unit 5 through manual operation of the joystick 4.

Hereinafter, a description of the position detection unit 300 arranged to detect whether or not the mobile base 3 is placed at a position such that the alignment in the fully automatic mode can be performed. The position detection unit 300 is used for detecting whether or not the mobile base 3 is placed at a predetermined position on the main base 1, which is predetermined for the purpose of fully automatic control.

Figure 5:
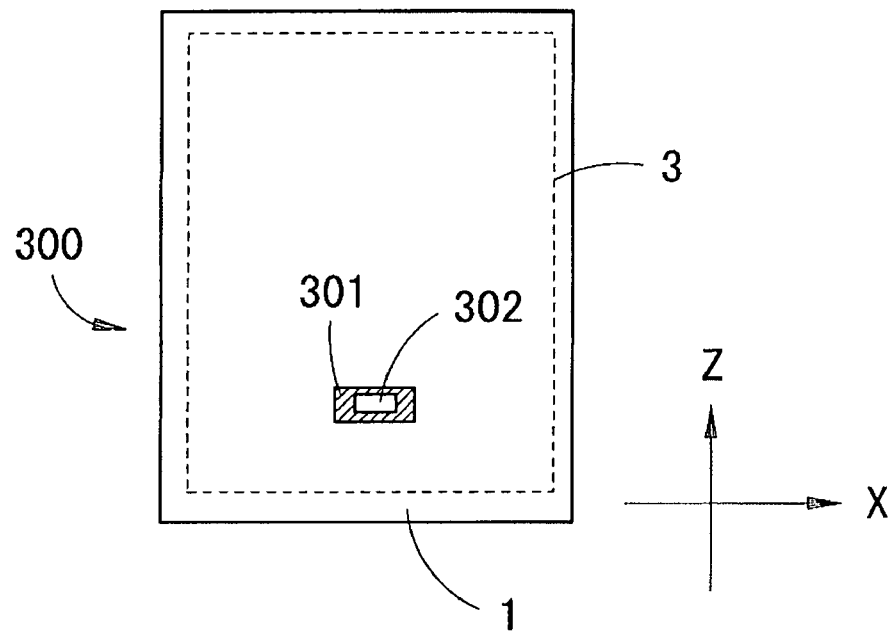
FIG. 5 is a view showing a specific configuration of a position detection unit of the ophthalmic apparatus.

FIG. 5 is a view showing a specific configuration of the position detection unit 300. For the position detection unit 300, a shielding plate 301 which is provided on the main base 1 and a photosensor 302 comprising a projection portion and a photo-receiving portion which is provided to a bottom face portion of the mobile base 3 are used. When the mobile base 3 is placed in the vicinity of a center position in the movable range in the x-direction of the mobile base 3 while placed behind a given position (at the examiner's side) in the movable range in the Z-direction of the mobile base 3, the positions of the shielding plate 301 and the photosensor 302 in the X- and Z-directions correspond with each other. When the mobile base 3 goes beyond the above-described range, the positions of the shielding plate 301 and the photosensor 302 deviate in the X- and Z-directions from each other.

When the photosensor 302 is placed on the shielding plate 301, light emitted from the projection portion is absorbed in the shielding plate 301 and does not reach the photo-receiving portion, and accordingly a photo-receiving signal from the photosensor 302 is not outputted. Based on this, the control unit 70 detects that the mobile base 3 is placed at the predetermined position which is predetermined for the purpose of the fully automatic control. Meanwhile, when the photosensor 302 is not placed on the shielding plate 301, the light emitted from the projection portion is reflected by the main base 1 and reaches the photo-receiving portion, and accordingly a photo-receiving signal from the photosensor 302 is outputted. Based on this, the control unit 70 detects that the mobile base 3 is not placed at the predetermined position. The position detection unit 300 is not limited to the above-described configuration, and for the position detection unit 300, a micro-switch is preferably used, or a potentiometer or other detecting elements are preferably used such that the position detection is made based on a result which is detected as the need arises.

In a case where the position of the mobile base 3 is predetermined for the purpose of the fully automatic control as described above, it is necessary to predetermine the position considering ability of the alignment in the X- and Z-directions of the ophthalmic examination unit 5 with respect to the eyes through the driving of the XZ driving unit 7, possibility of contact of the ophthalmic examination unit 5 moved by the XZ driving unit 7 with the examinee, possibility of contact of the ophthalmic examination unit 5 moved by the XZ driving unit 7 with the face supporting unit 10 and other factors in the state of the mobile base 3 locked by the lock mechanism 200.

Therefore, as the position of the mobile base 3 for the purpose of the fully automatic control, considered is a position such that the alignment of the ophthalmic examination unit 5 which is moved in X- and Z-directions with respect to the locked mobile base 3 can be performed with respect to each eye in sequence and that the ophthalmic examination unit 5 is not brought into contact with any of the eyes at a limited position for forward movement of the ophthalmic examination unit 5.

To be specific, for the predetermined position in the Z-direction of the mobile base 3, considered is a position such that the alignment in the Z-direction of the ophthalmic examination unit 5 with respect to the eyes can be performed within the movable range of the ophthalmic examination unit 5 by the XZ driving unit 7 and that the ophthalmic examination unit 5 is not brought into contact with the examinee when moved to the forefront of the movable range of the ophthalmic examination unit 5 by the XZ driving unit 7 while the mobile base 3 is locked by the lock mechanism 200. For example, the position is predetermined within a range from a center position to a rearmost position in the movable range in the Z-direction of the mobile base 3. In the preferred embodiment of the present invention, a position at a rearmost edge in the movable range in the Z-direction of the mobile base 3 is predetermined as the predetermined position.

The operation of the apparatus having the above-described configuration is described. The control unit 70 detects the lock of the mobile base 3 by the lock mechanism 200 based on the detection signal from the lock detection unit 250. Then, the control unit 70 permits the XZ driving unit 7 to move the ophthalmic examination unit 5 in the fully automatic mode, controls the Y driving unit 6 and the XZ driving unit 7 to move the ophthalmic examination unit 5 and performs the alignment of the ophthalmic examination unit 5 with respect to each eye in sequence while the mobile base 3 is locked, and performs measurement of both the eyes.

To be specific, when power of the apparatus is turned on, the control unit 70 judges whether or not the mobile base 3 is locked to the fixed main base 1 based on the detection signal from the lock detection unit 250. In addition, the control unit 70 judges whether or not the mobile base 3 is placed at the above-described predetermined position which is predetermined for the alignment in the fully automatic mode based on a detection signal from the position detection unit 300. That is, the control unit 70 judges whether or not the mobile base 3 is locked to the fixed main base 1 at the predetermined position.

In addition, the control unit 70 displays a message that whether or not the mobile base 3 is in a lock state and whether or not the mobile base 3 is placed at the position predetermined for the alignment in the fully automatic mode based on the detection signals from the lock detection unit 250 and the position detection unit 300.

In order for the examiner to bring the apparatus into a state where the alignment in the fully automatic mode is possible, it is essential only that the examiner should move the mobile base 3 to the predetermined position using the joystick 4 so that the message that the mobile base 3 is placed at the position predetermined for the alignment in the fully automatic mode is displayed, and then lock the mobile base 3 using the lock mechanism 200.

When detecting that the mobile base 3 is locked to the main base 1 at the predetermined position, the control unit 70 emits a signal for permitting the operation of the alignment in the fully automatic mode. In addition, the control unit 70 controls the display monitor 8 to display a message (inform) that the alignment in the fully automatic mode is possible. That is, when the mobile base 3 is locked to the fixed main base 1 at the predetermined position, the control unit 70 permits the XZ driving unit 7 to move the ophthalmic examination unit 5 in the fully automatic mode, and automatically switches the alignment mode to the fully automatic mode. In this case, when the movement of the mobile base 3 is brought to the state of being locked by the lock mechanism 200, the mobile base 3 does not move horizontally even if the examiner performs tilting operation of the joystick 4.

In addition, when detecting that the mobile base 3 is locked to the fixed main base 1 at the predetermined position, the control unit 70 drives and controls the Y driving unit 6 and the XZ driving unit 7 to move the ophthalmic examination unit 5 to its original position which is predetermined. For the original position in the X-direction of the ophthalmic examination unit 5, an almost center position in the movable range of the ophthalmic examination unit 5 is predetermined, and for the original position in the Z-direction of the ophthalmic examination unit 5, a position closest to the examiner is predetermined.

In the above-described operation, it is also preferable that the control unit 70 switches the mode when the mode changeover switch provided to the control section 9a is operated and a signal for switching to the fully automatic mode is inputted, and permits the XZ driving unit 7 to move the ophthalmic examination unit 5 in the fully automatic mode when the lock detection unit 250 and the position detection unit 300 detect that the mobile base 3 is locked at the predetermined position.

In the state where the fully automatic mode is established as described above, the examiner first fixes the examinee's face to the face supporting unit 10. Then, when operation of a predetermined switch (operation of pressing the measurement starting switch 4b) is performed by the examiner, the control unit 70 starts, based on a signal of the operation, the automatic alignment operation with respect to the eyes of the examinee whose face is fixed to the face supporting unit 10. The control unit 70 firstly detects the positions of the eyes based on the broad anterior-segment image (the low magnification image) which is obtained by the two-dimensional photodetector 52 and, based on information of the positions, performs height adjustment of the chin rest 12 and alignment adjustment in the up/down and right/left directions with respect to the eyes. In addition, the control unit 70 controls the display monitor 8 to display the broad anterior-segment image obtained by the two-dimensional photodetector 52 (see FIG. 6).

To be specific, the control unit 70 extracts black portions of pupils of the eyes by retrieving light and shade information from the image obtained by the two-dimensional photodetector 52 and, based on the black portions, detects the positions of the eyes. Then, when the positional information of the eyes is detected, the control unit 70 controls the motor 24 of the chin rest movement mechanism 30 to move the chin rest 12 so as to bring the height of the eyes to the same level as the eye level markers 14 (for the details, see Japanese Patent Application Unexamined Publications Nos. 2004-174155 and 2006-280612 and other references). In this case, it is also preferable that the height adjustment of the chin rest 12 is performed based on an operation signal from the chin rest switch 9b operated by the examiner.

In addition, the control unit 70 finds a deviation amount of each of the eyes with respect to the ophthalmic examination unit 5 based on the positional information of the eyes, and controls the ophthalmic examination unit to move in the X- and Y-directions to the right eye which is the first measurement eye (this is determined in advance) based on information of the deviation amounts. Thus, the measurement optical axis L1 of the ophthalmic examination unit 5 is positioned in the vicinity of the right eye, which allows the examinee to visually perceive a fixation target with the right eye, so that the fixation target is fixated with the right eye.

When the rough alignment in the X- and Y-directions is completed, the alignment detection is switched to target detection by the two-dimensional photodetector 65, and an alignment state of the ophthalmic examination unit 5 with respect to the eye is detected by detecting the alignment target image projected onto the cornea. At this time, the Z-direction of the ophthalmic examination unit 5 is deviated in a direction apart from its appropriate operating distance, so that the alignment target image is detected while the ophthalmic examination unit 5 is moved forward to the eye. In addition, the control unit 70 controls the display monitor 8 to display the anterior-segment image under high magnification by the two-dimensional photodetector 65 (see FIG. 7).

At this stage, the control unit 70 finds alignment deviation amounts in the X- and Y-directions of the ophthalmic examination unit 5 assuming a center position of a ring target image R which is picked up by the two-dimensional photodetector 65 as a corneal vertex position M0. Then, the control unit 70 controls and drives, based on the deviation amounts, the Y driving unit 6 and the XZ driving unit 7 to move the ophthalmic examination unit 5 in the X- and Y-directions. In addition, utilizing the characteristic that a space of the ring target image R in a predetermined meridian direction varies while a space between infinite target images M little varies, the control unit 70 finds an alignment deviation amount in the Z-direction of the ophthalmic examination unit 5 with respect to the eye (for the details, see Japanese Patent Application Unexamined Publications No. Hei06-46999 corresponding to U.S. Pat. No. 5,463,430). Then, the control unit 70 controls and drives, based on the deviation amount, the XZ driving unit 7 to move the ophthalmic examination unit 5 in the Z-direction. When the alignment deviation amounts in the X-, Y- and Z-directions with respect to the eye reach given permissible ranges in the respective directions in this manner, the control unit 70 judges the alignment state of the ophthalmic examination unit 5 with respect to the eye as appropriate. Thereafter, the control unit 70 emits the trigger signal for starting examination and starts the examination of the eye through the operation of the ophthalmic examination optical system.

After the completion of the measurement of the right eye, the control unit 70 controls, based on the information of the distance between the right and left eyes, to move the ophthalmic examination unit 5 in the X- and Y-directions such that the left eye is positioned in the vicinity of the measurement optical axis L1. Then, in the same manner as the right eye, the control unit 70 controls and drives, based on a signal from the image picked up by the two-dimensional photodetector 65, the Y driving unit 6 and the XZ driving unit 7, completes the precise alignment of the eyes and automatically performs the measurement. For the details of control of performing automatic alignment based on a result of an image of examinee's eyes which is picked up in advance, see Japanese Patent Application Unexamined Publications No. Hei10-216089.

After a result of the examination of the examinee's eyes is thus obtained, the control unit 70 controls the display monitor 8 to display the measurement result while driving and controlling the Y driving unit 6 and the XZ driving unit 7 to return the ophthalmic examination unit 5 to its original position.

By returning the ophthalmic examination unit 5 to its original position, it is made possible that the alignment with respect to the eyes is properly performed while the ophthalmic examination unit 5 which is moved in the wide area by the XZ driving unit 7 is prevented from being brought into contact with the examinee (or the face supporting unit 10) when the alignment in the fully automatic mode is performed while the mobile base 3 is locked by the lock mechanism 200.

Next, the operation in the manual mode will be described. When detecting that the mobile base 3 is unlocked by the lock mechanism 200 based on the detection signal from the lock detection unit 250, the control unit 70 prohibits the XZ driving unit 7 to move the ophthalmic examination unit 5 in the fully automatic mode.

To be specific, the control unit 70 emits a signal for permitting the alignment in the manual mode when judging that the mobile base 3 is unlocked from the main base 1 based on the detection signals from the position detection unit 300 and the lock detection unit 250 (or, that the mobile base 3 is deviated from the predetermined position in the X- and Z-directions such that the alignment in the fully automatic mode can be performed). In addition, the control unit 70 controls the display monitor 8 to display a message (inform) that the alignment in the manual mode is possible. In addition, the control unit 70 displays the message that whether or not the mobile base 3 is in the lock state and whether or not the mobile base 3 is placed at the position predetermined for the alignment in the fully automatic mode. At this time, when the mobile base 3 is brought to the state of being unlocked by the lock mechanism 200, the mobile base 3 is brought to a state of being movable horizontally with respect to the main base 1 through tilting operation of the joystick 4 by the examiner.

In addition, when detecting that the mobile base 3 is unlocked by the lock mechanism 200, the control unit 70 drives and controls the Y driving unit 6 and the XZ driving unit 7 to move the ophthalmic examination unit 5 to its original position which is predetermined. For the original position in the X- and Y-directions of the ophthalmic examination unit 5, an almost center position in the movable range of the ophthalmic examination unit 5 is predetermined, and for the original position in the Z-direction of the ophthalmic examination unit 5, a position which is located in front by a given distance of a rearmost edge in the movable range is predetermined considering a traveling space in the back direction of the ophthalmic examination unit 5 by the XZ driving unit 7 in the second manual mode. For example, a position which is located 5 mm in front of the rearmost edge is preferably predetermined. Alternatively, a position which is located at an almost center position in the movable range in the Z-direction is preferably predetermined.

The examiner can make a selection between the first manual mode and the second manual mode with the use of a given mode-selecting switch which is provided to the control section 9a (it is also preferable that the selection is made in advance by parameter setup). When the first manual mode is established, the control unit 70 prohibits the driving of the XZ driving unit 7 and controls the ophthalmic examination unit 5 to be fixed to the mobile base 3. When the second manual mode is established, the control unit 70 limits a driving range of the XZ driving unit 7 and controls the ophthalmic examination unit 5 to move only within the range which is predetermined with reference to the original position. In other words, the control unit 70 limits the movable range of the ophthalmic examination unit 5 by the XZ driving unit 7 and prohibits the ophthalmic examination unit 5 to move beyond the range predetermined with reference to the original position. For example, in order to perform precise alignment by driving and controlling the Y driving unit 6 and the XZ driving unit 7 based on the alignment detection, the ophthalmic examination unit 5 is arranged to be movable 5 mm both in the back direction and the forth direction from the original position in the Z-direction and movable 5 mm both in the right direction and the left direction from the original position in the X-direction.

When the manual mode is established as described above, the examiner instructs the examinee to rest the chin on the chin rest 12, and the chin of the examinee is rested thereon. At this time, when the micro-switch 305 detects that the mobile base 3 is moved in a given position in the back and forth direction, the control unit 70 controls the display monitor 8 to display the image obtained by the two-dimensional photodetector 52. When the broad image is displayed on the display monitor 8 as shown in FIG. 6, the examiner adjusts the height of the chin rest 12 so as to bring the height of the eyes to the same level as the eye level markers 14 which are displayed on the display monitor 8. In this case, the control unit 70 drives the motor 24 to move up and down the chin rest 12 based on the operation signal from the chin rest switch 9b operated by the examiner. It is also preferable that the height of the chin rest 12 is automatically adjusted so as to bring the height of the eyes to the same level as the eye level markers 14 based on the broad anterior-segment image.

If the broad image is not displayed on the display monitor 8, the joystick 4 is tilted in the back direction repeatedly until the image on the display monitor 8 is switched to the broad image and then the chin rest 12 is moved up and down as described above, which allows the adjustment of the eye level of the examinee to be performed. Thus, the examinee's face is firmly fixed to the face supporting unit 10, which allows precise measurement or photographing. After the completion of the adjustment of the eye level in the above-described manner, it is preferable that the examiner adjusts the position in the X- and Y-directions of the ophthalmic examination unit 5 with respect to the eyes using the joystick 4 and the rotation knob 4a so that the eyes and a reticle mark LT in the broad image nearly coincide with each other because subsequent alignment work is made easy.

Then, the examiner tilts the joystick 4 in the forth direction and brings the ophthalmic examination unit 5 close to the eyes in order to adjust a working distance between the eyes and the ophthalmic examination unit 5. Thus, the mobile base 3 is moved forward, and the control unit 70 detects that the mobile base 3 is deviated from the given position in the back and forth direction and accordingly switches the image displayed on the display monitor 8 from an output of the second photographing optical system 50 to an output of the first photographing optical system 60. Thus, the displayed anterior-segment image is switched from the broad image to the magnified anterior-segment image.

In this state, the examiner instructs the examinee to fixate the fixation target (not shown) and performs the alignment adjustment with respect to the examinee's eye with the use of the joystick 4. If a clear image of the eye with no blur appears on the display monitor 8, the examiner performs fine alignment of the position in the up/down and right/left directions of the ophthalmic examination unit 5 with respect to the eye so that the ring target image R and a reticle mark LT displayed on the display monitor 8 become concentric circles. After that, the examiner performs fine alignment of the position in Z-direction of the ophthalmic examination unit 5 referring to an indicator (not shown) (or, such that the ring target image R becomes the thinnest). Then, the examiner presses the measurement starting switch 4b after the completion of the alignment, and the measurement by the ophthalmic examination optical system 5b is performed (the first manual mode). In the case of the second manual mode, when the alignment fixation target becomes detected by the two-dimensional photodetector 65, the control unit 70 detects the alignment state of the ophthalmic examination unit 5 with respect to the eye based on the position of the alignment fixation target image which is photo-received on the two-dimensional photodetector 65 and, based on a result of the detection, drives and controls the Y driving unit 6 and the XZ driving unit 7. Then, after the completion of the alignment, the control unit 70 emits the trigger signal for starting measurement based on an alignment-completion signal from the control unit 70 or the trigger signal from the measurement starting switch 4b.

In the above-described manual mode, if it is arranged that the images photographed by the second photographing optical system 50 and the first photographing optical system 60 are selectively displayed on the display monitor 8 based on the movement in the back/forth direction of the mobile base 3 moved by the sliding mechanism, the detection signal from the position detection unit 300 is preferably used. In the above-described configuration, the position at the rearmost edge in the Z-direction is predetermined as the predetermined position in the back/forth direction; however, the predetermined position is not limited thereto if the mobile base 3 is located at a position which is beyond the range in the back/forth direction of the mobile base 3 which is required for the alignment of the ophthalmic examination unit 5 with respect to the eye with the use of the first photographing optical system 60. To be specific, if the mobile base 3 is movable about 40 mm in the back/forth direction with respect to the fixed main base 1 by the sliding mechanism, by establishing a range from a forefront position which is the closest to the eye to a position 30 mm therefrom as the movable range of the mobile base 3 in the back/forth direction which is required to perform the alignment with the use of the first photographing optical system 60, a position posterior to the established range is preferably predetermined as the predetermined position.

In the case of starting the alignment operation with respect to the eye in the fully automatic mode, it is also preferable that with a sensor for an examinee provided which detects whether or not the examinee's face is fixed to the face supporting unit 10, the alignment operation with respect to the eye is started when the sensor detects that the examinee's face is fixed thereto while it is detected that the mobile base 3 is locked at the predetermined position which is predetermined for the alignment in the fully automatic mode. For the sensor, a touch sensor which is provided on the chin rest unit 12 and a distance measurement sensor which is provided to the face supporting unit 10 are preferably used (see Japanese Patent Application Unexamined Publication No. 2005-211351).

In the above descriptions, whether the mobile base 3 is placed at the predetermined position which is predetermined for the alignment in the fully automatic mode is checked by seeing the display of the display monitor 8; however, this is not limited thereto. It is also preferable that with a marking provided to the main base 1 or the mobile base 3, the examiner checks whether the mobile base 3 is placed at the predetermined position which is predetermined for the alignment in the fully automatic mode while seeing the marking. It is also preferable to arrange that the examiner feels a click when the mobile base 3 is placed at the predetermined position which is predetermined for the alignment in the fully automatic mode.

In the above descriptions, the predetermined position which is predetermined for the alignment in the fully automatic mode is arranged to have the range to some extent; however, this is not limited thereto. It is also preferable that the position of the mobile base 3 which is locked by a stopper mechanism is predetermined as the position which is predetermined for the alignment in the fully automatic mode by using a configuration such that after placing the mobile base 3 at the laterally almost center of the main base 1, the examiner pulls the stopper mechanism toward the examiner to actuate the stopper mechanism and thereby the mobile base 3 is locked (see Japanese Patent Application Unexamined Publication No. Hei08-280627 corresponding to U.S. Pat. No. 5,689,325).

Concerning the fully automatic mode, it is also preferable that when the position detection unit 300 detects that the mobile base 3 is placed at the predetermined position and the fully automatic mode is established, the control unit 70 starts the driving of the Y driving unit 6 and the XZ driving unit 7 based on a predetermined trigger signal and performs the alignment of the ophthalmic examination unit 5 with respect to each right and left eye in sequence. It is also preferable that the control unit 70 stops the driving of the XZ driving unit 7 when the position detection unit 300 detects that the mobile base 3 deviates from the predetermined position during the driving of the XZ driving unit 7 in the fully automatic mode.

In addition, in the fully automatic mode, it is also preferable that the position of the mobile base 3 in a state where the rough alignment of the ophthalmic examination unit 5 with respect to one of the eyes through the movement of the mobile base 3 is completed is predetermined as a predetermined position. In this case, after the rough alignment with respect to the eye is performed by the examiner, the control unit 70 starts the driving of the Y driving unit 6 and the XZ driving unit 7 based on the above-described alignment detection result, and performs the fine alignment with respect to the eye. Then, the control unit 70 controls the driving of the Y driving unit 6 and the XZ driving unit 7 to perform the rough alignment and the fine alignment with respect to the other eye. When the rough alignment with the other eye is performed, the control unit 70 preferably controls the driving of the XZ driving unit 7 to move the ophthalmic examination unit 5 toward the eye until the alignment target image is detected by the two-dimensional photodetector 65. It is also preferable that with a detection mechanism provided for detecting a movement amount of the mobile base 3 (or the ophthalmic examination unit 5) with respect to the lateral center position of the main base 1, the ophthalmic examination unit 5 is moved toward the eye by two times of the movement amount detected by the detection mechanism when the alignment with respect to the first eye is completed.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An ophthalmic apparatus comprising:
    an ophthalmic examination unit arranged to perform examination of an examinee's eye;
    an alignment state detection unit arranged to detect an alignment state of the ophthalmic examination unit with respect to the eye, the alignment state detection unit comprising a photographing optical system arranged to photograph an anterior segment of the eye and placed in the ophthalmic examination unit;
    a main base;
    a mobile base on which the ophthalmic examination unit is mounted, the mobile base arranged to be moved in a horizontal direction on the main base through operation of a control member by an examiner;
    a vertical driving mechanism arranged to move the ophthalmic examination unit vertically with respect to the mobile base through driving of a motor;
    a horizontal driving mechanism arranged to move the ophthalmic examination unit horizontally with respect to the mobile base through driving of a motor, a movable range in a right/left direction of the horizontal driving mechanism being established to be more than a predetermined pupillary distance;
    mode changeover means arranged to switch a mode between a manual mode of performing alignment of the ophthalmic examination unit with respect to each right and left eye in sequence through the operation of the control member, and a fully automatic mode of performing the alignment through driving of the driving mechanisms; and a control unit arranged to control the driving of the driving mechanisms based on a detection result by the alignment state detection unit, wherein the control unit starts, in a case where the fully automatic mode is established by the mode changeover means, the driving of the driving mechanisms based on a predetermined trigger signal which is emitted when the mobile base is placed at a predetermined position on the main base so as to perform the alignment.

2. The ophthalmic apparatus according to claim 1, further comprising a position detection sensor arranged to detect whether the mobile base is placed at the predetermined position, wherein the control unit starts, in a case where the position detection sensor detects that the mobile base is placed at the predetermined position and the fully automatic mode is established by the mode changeover means, the driving of the driving mechanisms based on the predetermined trigger signal so as to perform the alignment.

3. The ophthalmic apparatus according to claim 2, further comprising:

a lock mechanism arranged to lock the mobile base to the main base; and a lock sensor arranged to detect that the mobile base is locked by the lock mechanism, wherein the control unit starts, in a case where the position detection sensor and the lock sensor detect that the mobile base is locked to the main base at the predetermined position and the fully automatic mode is established by the mode changeover means, the driving of the driving mechanisms based on the predetermined trigger signal so as to perform the alignment.

4. The ophthalmic apparatus according to claim 1, wherein the predetermined position of the mobile base is predetermined to be a position such that the alignment of the ophthalmic examination unit which is moved horizontally with respect the mobile base can be performed with respect to each eye in sequence and that the ophthalmic examination unit is not brought into contact with any of the eyes at a limited position for forward movement of the ophthalmic examination unit.

5. The ophthalmic apparatus according to claim 1, wherein the mode changeover means is arranged to switch the manual mode between a first manual mode of performing the alignment through the operation of the control member and a second manual mode of performing the alignment through the operation of the control member and the driving of the driving mechanisms, and the control unit starts, in a case where the second manual mode is established by the mode changeover means, the driving of the driving mechanisms based on the detection result by the alignment state detection unit after rough alignment of the ophthalmic examination apparatus is performed through the operation of the control member so as to perform fine alignment of the ophthalmic examination unit with respect to each eye.

* * * * *